United States Patent [19]

Hilfman

[11] 4,202,996
[45] May 13, 1980

[54] HYDROCARBON ISOMERIZATION PROCESS

[75] Inventor: Lee Hilfman, Mt. Prospect, Ill.

[73] Assignee: UOP Inc., Des Plaines, Ill.

[21] Appl. No.: 973,306

[22] Filed: Dec. 26, 1978

Related U.S. Application Data

[63] Continuation-in-part of Ser. No. 810,323, Jun. 27, 1977, Pat. No. 4,148,759, which is a continuation-in-part of Ser. No. 684,055, May 6, 1976, abandoned.

[51] Int. Cl.$^2$ ............................ C07C 5/24; C07C 5/26
[52] U.S. Cl. ..................................... 585/377; 585/477; 585/664; 585/666; 585/670; 585/671
[58] Field of Search ............ 260/666 P, 668 A, 683.2, 260/683.7; 585/377, 477, 664, 666, 670, 671

[56] References Cited

U.S. PATENT DOCUMENTS

| | | | |
|---|---|---|---|
| 3,304,339 | 2/1967 | Beuesi | 585/477 |
| 3,365,392 | 1/1968 | Mitsche et al. | 252/455 Z |
| 3,428,704 | 2/1969 | Fishel | 585/666 |
| 3,709,814 | 1/1973 | Jaffe | 252/455 Z |
| 3,723,556 | 3/1973 | Wilhelm | 585/670 |
| 3,839,486 | 10/1974 | Argaubright | 585/670 |

Primary Examiner—Veronica O'Keefe
Attorney, Agent, or Firm—James R. Hoatson, Jr.; John G. Cutts, Jr.; William H. Page, II

[57] ABSTRACT

Isomerizable hydrocarbons including paraffins, cycloparaffins, olefins and alkyl aromatics are isomerized by contacting the hydrocarbon at isomerization conditions with a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum.

12 Claims, 1 Drawing Figure

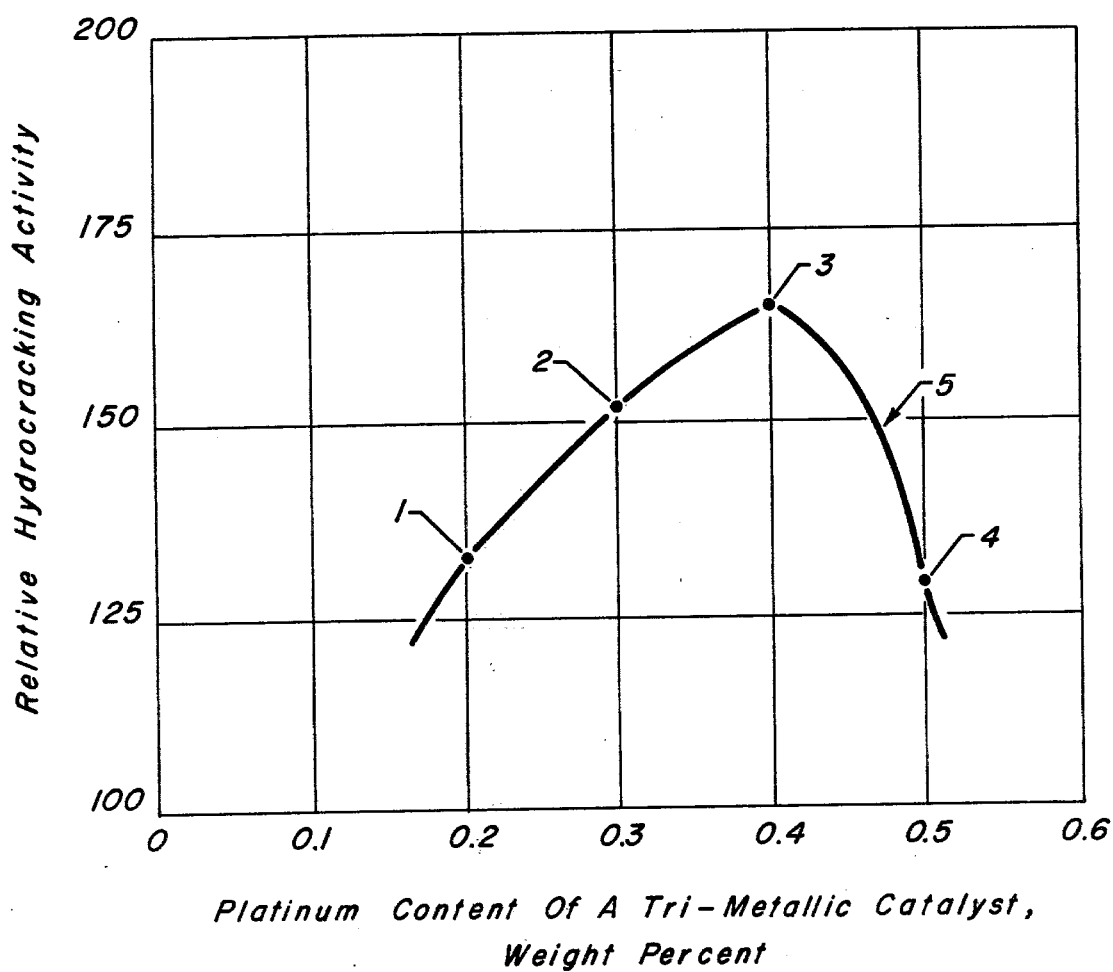

HYDROCARBON ISOMERIZATION PROCESS

CROSS-REFERENCE TO RELATED APPLICATIONS

This application is a continuation-in-part of my prior, copending application Ser. No. 810,323 filed on June 27, 1977 now U.S. Pat. No. 4,148,759 which is a continuation-in-part of my application Ser. No. 684,055 filed on May 6, 1976, now abandoned. The teachings of these prior applications are specifically incorporated herein by reference thereto.

BACKGROUND OF THE INVENTION

This invention relates to a process for isomerizing isomerizable hydrocarbons, and, in particular, isomerizable paraffins, cycloparaffins, olefins and alkylaromatics. More particularly, this invention relates to a process for isomerizing isomerizable hydrocarbons with a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum.

Isomerization processes for the isomerization of hydrocarbons have acquired significant importance within the petrochemical and petroleum refining industry.

The demand for the xylene isomers, particularly para-xylene, has resulted in the need for processes for isomerizing xylenes and ethylbenzene to obtain a desired xylene isomer such as para-xylene. Also, the need for branched chain paraffins such as isobutane or isopentane as intermediates for the production of high octane motor fuel produced by alkylation, it is desired that the final alkylate be highly branched. This can be accomplished by alkylating isobutane or isopentane with a $C_4$–$C_7$ internal olefin which, in turn, can be produced by the isomerization of the linear alpha-olefin by shifting the double bond to a more central position.

SUMMARY OF THE INVENTION

Accordingly, it is an object of this invention to provide a process for isomerizing isomerizable hydrocarbons. More specifically, it is an object of this invention to provide an isomerization process using a particular isomerization catalyst effective in isomerizing isomerizable hydrocarbons without introducing undesired decomposition reactions.

In a broad embodiment, this invention relates to a process for isomerizing an isomerizable hydrocarbon which comprises contacting said hydrocarbon with a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum.

In a more specific embodiment, this invention relates to the isomerization of either a saturated or olefinic isomerizable hydrocarbon by contacting the hydrocarbon with the aforementioned catalytic composite at isomerization conditions which include a temperature of about 0° C. to about 425° C., a pressure of about atmospheric to about 100 atmospheres, and a liquid hourly space velocity of about 0.1 to about 20.0 hr.$^{-1}$. In another limited embodiment, this process relates to the isomerization of an isomerizable alkylaromatic hydrocarbon by contacting an alkylaromatic with the aforementioned catalytic composite at isomerization conditions which include a temperature of about 0° C. to about 600° C., a pressure of about atmospheric to about 100 atmospheres, a liquid hourly space velocity of about 0.1 to about 20.0 hr.$^{-1}$ and a hydrogen to hydrocarbon mole ratio of about 0.5:1 to about 20:1.

In a more specific embodiment, the catalytic composite used in isomerizing the foregoing isomerizable hydrocarbons contains, on an elemental basis 0.1 to about 5 weight percent halogen and about 0.2 to about 0.5 weight percent platinum group metal.

In another embodiment, this invention relates to a catalytic composite which comprises a Friedel-Crafts metal halide component.

Other objects and embodiments referring to alternative isomerizable hydrocarbons and to alternative catalytic compositions will be found in the following further detailed description of this invention.

DETAILED DESCRIPTION

The process of this invention is applicable to the isomerization of isomerizable saturated hydrocarbons including acyclic paraffins and cyclic naphthenes and is particularly suitable for the isomerization of straight chain or mildly branched chain paraffins containing 4 or more carbon atoms per molecule such as normal butane, normal pentane, normal hexane, normal heptane, normal octane, etc., and mixtures thereof. Cycloparaffins applicable are those ordinarily containing at least 5 carbon atoms in the ring such as alkylcyclopentanes and cyclohexanes, including methylcyclopentane, dimethylcyclopentane, cyclohexane, methylcyclohexane, dimethylcyclohexane, etc. This process also applies to the conversion of mixtures of paraffins and/or naphthenes such as those derived by selective fractionation and distillation of straight-run natural gasolines and naphthas. Such mixtures of paraffins and/or naphthenes include the so-called pentane fractions, hexane fractions, and mixtures thereof. It is not intended to limit this invention to these enumerated saturated hydrocarbons, and it is contemplated that straight or branched chain saturated hydrocarbon containing up to about 20 carbon atoms per molecule may be isomerized according to the process of the present invention with $C_4$–$C_7$ n-alkanes being particularly preferred.

The olefins applicable within this isomerization process are generally a mixture of olefinic hydrocarbons of approximately the same molecular weight, including the 1-isomer, 2-isomer, and other position isomers, capable of undergoing isomerization to an olefin in which the double bond occupies a more centrally located position in the hydrocarbon chain. The process of this invention can be used to provide an olefinic feed stock for motor fuel alkylation purposes containing an optimum amount of the more centrally located double bond isomers, by converting the 1-isomer, or other near terminal position isomer into olefins wherein the double bond is more centrally located in the carbon atoms chain. The process of this invention is also applicable to the isomerization of such isomerizable olefinic hydrocarbons such as the isomerization of 1-butene to 2-butene or the isomerization of the 3-methyl-1-butene to 2-methyl-2-butene. Also, the process of this invention can be utilized to shift the double bond of an olefinic hydrocarbon such as 1-pentene, 1-hexene, 2-hexene, and 4-methyl-1-pentene to a more centrally located position so that 2-pentene, 2-hexene, 3-hexene and 4-methyl-2-pentene, respectively, can be obtained. It is not intended to limit this invention to these enumerated olefinic hydrocarbons as it is contemplated that shifting of the double bond to a more centrally located position may be effective in straight or branched chain olefinic hydrocarbons containing up to about 20 carbon atoms per molecule. Preferred are linear $C_4$–$C_7$ alpha-mono-olefins. The process of this invention also applies to the hydroisomerization of olefins wherein olefins are converted to branched-chain paraffins.

Further, the process of this invention is also applicable to the isomerization of isomerizable alkylaromatic hydrocarbons including ortho-xylene, meta-xylene, para-xylene, ethylbenzene, the ethyltoluenes, the trimethylbenzenes, the diethylbenzenes, the triethylbenzenes, normal propylbenzene, isopropylbenzene, etc., and mixtures thereof. Preferred isomerizable alkylaromatic hydrocarbons are the monocyclic alkylaromatic hydrocarbons, that is, the alkyl benzene hydrocarbons, particularly the $C_8$ alkylbenzenes, and nonequilibrium mixtures of the various $C_8$ aromatic isomers.

These foregoing isomerizable hydrocarbons may be derived as selective fractions from various naturally-occurring petroleum streams either as individual components or as certain boiling range fractions obtained by the selective fractionation and distillation of catalytically cracked gas oil. Thus, the process of this invention may be successfully applied to and utilized for complete conversion of isomerizable hydrocarbons when these isomerizable hydrocarbons are present in minor quantities in various fluid or gaseous streams. Thus, the isomerizable hydrocarbons for use in the process of this invention need not be concentrated. For example, isomerizable hydrocarbons appear in minor quantities in various refinery streams, usually diluted with gases such as hydrogen, nitrogen, methane, ethane, propane, etc. These refinery streams containing minor quantities of isomerizable hydrocarbons are obtained in petroleum refineries and various refinery installation including thermal cracking units, catalytic cracking units, thermal reforming units, coking units, polymerization units, dehydrogenation units, etc. Such refinery offstreams have in the past often been burned for fuel value, since an economical process for the utilization of the hydrocarbon content has not been available. This is particularly true for refinery fluid streams known as off gas streams containing minor quantities of isomerizable hydrocarbons.

As indicated in the embodiments, the catalyst utilized in the present isomerization process comprises a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum, and a halogen component.

I have discovered an improved catalyst comprising nickel-molybdenum-platinum on a zeolitic support or carrier material. More specifically, I have discovered that an unusually superior catalyst results if the platinum content is from about 0.2 to about 0.5 weight percent on an elemental basis. The cricicality of the range of the platinum concentration is further illustrated hereinbelow.

A particularly preferred catalyst support or base comprises a zeolite and alumina. In addition to the foregoing compositional limitations, it is important that the catalyst base have adequate pore volume, that is, a pore volume of at least 0.5 cc/g and preferably at least 0.6 cc/g or even 0.7 cc/g.

The zeolite-alumina catalyst base is preferably in the zerogel state, that is, it is dried sufficiently to afford the usual microporous structure and therefore an appreciable available surface.

In one embodiment, accordingly, the present invention provides a method of preparing catalytic composites having isomerization activity comprising the steps: (b) preparing a zeolite-alumina carrier material; (b) impregnating said zeolite-alumina carrier material with a nickel component, a molybdenum component and a platinum component in amounts sufficient to result in the composite containing, on an elemental basis, about 1 to about 15 weight percent nickel, about 1 to about 10 weight percent molybdenum and about 0.2 to about 0.5 weight percent platinum.

In another embodiment, the present invention relates to a process for isomerizing hydrocarbons which process comprises reacting said hydrocarbons with hydrogen in a reaction zone containing a catalytic composite prepared by a method comprising the steps: (a) preparing a zeolite-containing carrier material; (b) impregnating said carrier material with a nickel component, a molybdenum component and a platinum component in amounts sufficient to result in the composite containing, on an elemental basis, about 1 to about 15 weight percent nickel, about 1 to about 10 weight percent molybdenum and about 0.2 to about 0.5 weight percent platinum.

Other objects and embodiments of my invention relate to additional details regarding the preferred catalytic ingredients, the concentration of components within the catalytic composite, the method of catalyst preparation, preferred processing techniques and similar particulars which are herein set forth.

Catalytic composites, tailored for the conversion of hydrocarbonaceous material and particularly those intended for utilization in an isomerization process, have traditionally consisted of metallic elements chosen from Group VIII of the Periodic Table; however, metallic components from Group VIB are quite often incorporated therein.

I have found that a particularly effective zeolite-nickel-molybdenum-platinum hydrocracking catalyst can be prepared when the platinum content of the finished catalyst is maintained within the critical range of from about 0.2 to about 0.5 weight percent. Thus, it is now possible to prepare a more active and stable isomerization catalyst.

As is customary in the art of catalysis, when referring to the catalytically active metal, or metals, it is intended to encompass the existence of such metal in the elemental state or in some form such as an oxide, sulfide, halide, etc. Regardless of the state in which the metallic components actually exist, the concentrations are computed as if they existed in the elemental state.

The zeolite carrier material may be prepared and utilized as spheres, pills, pellets, extrudates, granules, etc. The carrier material may be prepared in any suitable manner and may be activated prior to use by one or more treatments including drying, calcination, steaming, etc. Although generally existing in some combined form, the concentration of the catalytically active metallic components is calculated on on the basis of the elemental metals. Suitable isomerization catalysts will contain from about 0.01% to about 30% by weight of one or more metals, or compounds thereof. Another constituent of isomerization catalysts is a halogen component. While the precise form of association of the halogen component of the carrier material is not accurately known, it is customary in the art to refer to the halogen component as being combined with the carrier or with the other ingredients of the catalyst therein. Combined halogen may be either fluorine, chlorine, iodine, bromine or mixtures thereof; of these, fluorine and chlorine are particularly preferred. The halogen will be composited with the carrier material in such a manner as results in a final catalytic composite containing from about 0.1% to about 2% by weight of a halogen component, calculated as the element.

The metallic components may be incorporated within the catalytic composite in any suitable manner including ion-exchange or impregnation of the carrier, and either after or before calcination. The preferred method for the incorporation of the metallic components is to impregnate the carrier material with an aqueous solution of nickel and molybdenum salts and then after drying and calcining, the platinum component is added with a separate impregnation with an aqueous solution of a chloroplatinic acid. Although the metallic components may be incorporated in any manner, it is believed that the two-step impregnation method hereinabove described yields a superior hydrocracking catalyst. Even though the reasons for such a superior catalyst are uncertain, it is believed that the incorporation of the platinum metal component subsequent to the incorporation of the molybdenum component results in the construction of the most favorable metallic clusters utilized in hydrocarbon conversion reactions.

Following the incorporation of the metallic components, the carrier material is dried and subjected to a high temperature calcination or oxidation technique at a temperature of about 750° F. to about 1000° F. One particularly preferred catalyst preparation technique involves the water-free reduction of the calcined composite. This particular step is designed to insure a more uniform and finely divided dispersion of the metallic components throughout the carrier material. Substantially pure and dry hydrogen, containing less than 30 volume ppm. of water is utilized as the reducing agent. The reduced catalytic composite may then subjected to a presulfiding technique to incorporate from about 0.05% to about 3.0% by weight of sulfur, on an elemental basis, within the final catalytic composite.

Although not essential, the resulting catalytic composite can be impregnated with an anhydrous Friedel-Crafts type metal halide, particularly aluminum chloride. Other suitable metal halides are aluminum bromide, ferric chloride, ferric bromide, zinc chloride, beryllium chloride, etc. This impregnation can be accomplished by the sublimination of the aluminum chloride onto the zeolite-alumina composite under conditions such that the sublimed aluminum chloride is chemically combined with the composite. This reaction is accompanied by the elimination of from about 0.5 to about 2.0 moles of hydrogen chloride per mole of aluminum chloride reacted. Since aluminum chloride sublimes at about 184° C. suitable impregnation temperatures range from about 190° C. to about 700° C.; preferably, 200° C. to about 600° C. The sublimation can be conducted at atmospheric pressure or under increased pressures and in the presence of diluents such as inert gases, hydrogen and light paraffinic hydrocarbons. The impregnation may be conducted batchwise but a preferred method is to pass sublimed $AlCl_3$ vapors in admixture with an inert gas such as $H_2$ through the calcined catalyst bed. This method both continuously deposits the $AlCl_3$ and removes the evolved HCl.

The amount of metal halide combined with the catalytic composite may range from about 5 to about 100 weight percent of the original composite. The final composite has unreacted metal halide removed by treating the composite at a temperature about 300° C. for a time sufficient to remove therefrom any unreacted metal halide. For aluminum chloride, temperatures of about 400° C. to about 600° C. and times of from about 1 to about 48 hours are satisfactory. The reaction of the aluminum chloride with the zeolite-alumina composite yields—$Al-O-AlCl_2$ active centers which can enhance the performance characteristics of the original catalytic composite.

According to the present invention, the isomerizable hydrocarbon, in admixture with hydrogen, is contacted with a catalyst of the type described above in a hydrocarbon conversion zone. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use a fixed bed system. In this system a hydrogen-rich gas and the charge stock are preheated by any suitable heating means to the desired reaction temperature and then are passed into a conversion zone containing a fixed bed of the catalyst type previously characterized. It is, of course, understood that the conversion zone may be one or more separate reactors with suitable means therebetween to insure that the desired conversion temperature is maintained at the entrance to each reactor. It is also to be noted that the reactants may be contacted with the catalyst bed in either upward, downward, or radial flow fashion. In addition, it is to be noted that the reactants may be in the liquid phase, a mixed liquid-vapor phase, or a vapor phase when they contact the catalyst, with best results obtained in the vapor phase.

The process of this invention, utilizing the catalyst hereinbefore set forth, for isomerizing isomerizable olefinic or saturated hydrocarbons is preferably effected in a continuous flow, fixed bed system. One particular method is continuously passing the hydrocarbon to a reaction zone containing the catalyst and maintaining the zone at proper isomerization conditions such as a temperature in the range of about 0° to about 425° C. or more, and a pressure of about atmospheric to about 200 atmospheres or more. The hydrocarbon is passed over the catalyst at a liquid hourly space velocity (defined as volume of liquid hydrocarbon passed per hour per volume of catalyst) of from about 0.1 to about 20 hr.$^{-1}$ or more. In addition, diluents such as argon, nitrogen, or hydrogen may be present. In fact, the presence of hydrogen at a hydrogen to hydrocarbon mole ratio of about 0.1:1 to about 10:1 is preferred. The isomerized product is continuously withdrawn, separated from the reactor effluent, and recovered by conventional means, preferably fractional distillation, while the unreacted starting material may be recycled to form a portion of the feed stock.

Likewise, the process of this invention for isomerizing an isomerizable alkylaromatic hydrocarbon is also preferably effected by passing the aromatic to a reaction zone containing the hereinbefore described catalyst and maintaining the zone at proper alkylaromatic isomerization conditions such as a temperature in the range of about 0° C. to about 600° C. or more, and a pressure of atmospheric to about 100 atmospheres or more. The hydrocarbon is passed, in admixture with hydrogen, at a liquid hourly hydrocarbon space velocity of about 0.1 to about 20 hr.$^{-1}$ or more and a hydrogen to hydrocarbon mole ratio of about 0.5:1 to about 20:1. Other inert diluents such as nitrogen, argon, etc. may also be present. The isomerized product is continually withdrawn, separated from the reactor effluent by conventional means such as fractional distillation or crystallization, and recovered.

Although the method of preparing the catalyst, and careful selection of operating conditions within the ranges hereinbefore set forth, extend the effective life of the catalyst composite, regeneration thereof may eventually become desired due to the natural deterioration of the catalytically active metallic components. The catalytic composite is readily regenerated by treating the same in an oxidizing atmosphere, at a temperature of from about 750° F. to about 850° F., and burning coke and other heavy hydrocarbonaceous material therefrom. The catalyst composite may then be subjected to the reducing in hydrogen, in situ, at a temperature up to about 1000° F. If desirable, the catalyst may then be sulfided in the same manner as fresh catalyst as hereinbefore described.

The drawing included in the instant application is for the purpose of visually demonstrating the improvements and advantages afforded by the manufacture of zeolite-nickel-molybdenum-platinum catalyst according to the present invention.

The following examples are presented in illustration of the catalyst of this invention and is not intended as an undue limitation on the generally broad scope of the invention as set out in the appended claims.

EXAMPLE I

This example describes the preparation and testing of four zeolite-nickel-molybdenum-platinum catalysts each of which has an extruded carrier material containing 25% alumina and 75% faujasite, 5% nickel, 2% molybdenum and which contain 0.2, 0.3, 0.4 and 0.5 weight percent platinum, respectively. The extruded alumina-faujasite carrier material was initially impregnated with an aqueous solution containing soluble nickel and molybdenum salts in sufficient concentration to yield a finished catalyst with the desired nickel and molybdenum concentrations. The freshly impregnated support was then dried at about 100° C. and calcined at about 500° C. The resulting dried and calcined carrier material containing 5% nickel and 2% molybdenum was divided into five batches and four batches were impregnated with an aqueous chloroplatinic acid solution with a concentration sufficient to yield a finished catalyst with 0.2, 0.3, 0.4 and 0.5 weight percent platinum, respectively. The platinum impregnated catalysts were then dried and calcined at 100° C. and 500° C., respectively. The fifth batch was not impregnated with platinum and served as a reference catalyst for comparison purposes.

A portion of each of the five hereinabove described batches of catalyst was then used in the hydrocracking of a vacuum gas oil whose properties are summarized in Table I.

TABLE I

| PROPERTIES OF VACUUM GAS OIL | | |
|---|---|---|
| API° Gravity at 60° F. | | 33.5 |
| Distillation, °F. | | |
| | IBP | 290 |
| | 10 | 455 |
| | 30 | 596 |
| | 50 | 697 |
| | 70 | 762 |
| | 90 | 830 |
| | 95 | 870 |
| | E.P. | 930 |
| | % Over | 99 |
| Total Sulfur, wt. % | | 0.22 |
| Total Nitrogen, ppm. | | 3 |

In each case, the vacuum gas oil was processed with a reactor pressure of 1500 psig., a liquid hourly space velocity of 2.0, a hydrogen circulation rate of 10,000 scf./bbl. and at a peak catalyst bed temperature of 315° C.

The hydrocracking ability of the non-platinum containing reference catalyst was arbitrarily assigned a Relative Hydrocracking Activity of 100. Platinum containing catalysts comprising 0.2, 0.3, 0.4 and 0.5 weight percent platinum and hereinafter referred to as Catalysts 1, 2, 3, and 4, respectively, were utilized to hydrocrack the hereinbefore described vacuum gas oil and these four catalysts exhibited a Relative Hydrocracking Activity of 133, 152, 165, and 129, respectively. These data are presented in tabular form in Table II and in graphical form in the accompanying drawing.

TABLE II

| EVALUATION FOR HYDROCRACKING ACTIVITY | | | | |
|---|---|---|---|---|
| Catalyst Identity | 1 | 2 | 3 | 4 |
| Platinum Concentration, wt. % | 0.2 | 0.3 | 0.4 | 0.5 |
| Relative Hydrocracking Activity | 133 | 152 | 165 | 129 |

From the data presented in foregoing Table II and with reference to the accompanying drawing, it will be seen that the four catalyst' increasing concentrations of platinum, the latter ranging from 0.2% to 0.5% by weight, did not demonstrate linearly increasing Relative Hydrocracking Activity. This is clearly brought out upon comparing the results obtained through the use of Catalysts 1, 2, 3 and 4 which indicated a Relative Hydrocracking Activity of 133, 152, 165 and 129 respectively, for the conversion of vacuum gas oil to lower boiling hydrocarbons. Datum points 1, 2, 3 and 4 in the drawing are representative of the results obtained with Catalysts 1, 2, 3 and 4, respectively. These data were employed in preparing curve 5 of the drawing, which curve clearly illustrates the criticality attached to the platinum concentration within the range of about 0.2% to about 0.5% by weight, in order to produce a hydrocracking catalyst with superior performance characteristics. The additional economic advantages afforded through this particular result will be readily recognized by those possessing skill within the art of petroleum refining processes.

EXAMPLE II

This example describes the preparation and testing of three zeolite-nickel-molybdenum-platinum catalysts each of which has an extruded carrier material containing 25% alumina and 75% faujasite, 5% nickel, 2% molybdenum and which contain 0.2 wt. % platinum, 0.5 wt. % platinum and 0.4 wt. % palladium, respectively.

The extruded alumina-faujasite carrier material was prepared in exactly the same manner as hereinabove described in Example I. The 5% nickel and 2% molybdenum was incorporated with said carrier material, also, as hereinabove described in Example I. Two portions of the resulting dried and calcined carrier material containing 5% nickel and 2% molybdenum were impregnated with an aqueous chloroplatinic acid solution with a concentration sufficient to yield a finished catalyst with 0.2 and 0.5 wt. % platinum, respectively. A third portion of the dried and calcined carrier material containing 5% nickel and 2% molybdenum was impregnated with an aqueous solution containing palladium chloride with a concentration sufficient to yield a finished catalyst with 0.4 wt. % palladium. Each of the three portions of the impregnated catalysts were then dried and calcined at 100° C. and 500° C., respectively.

The three portions of catalyst prepared as hereinabove described were then used in the hydrocracking of a vacuum gas oil whose properties are summarized in Table I. In each case, the gas oil was processed with a reactor pressure of 1500 psig., a liquid hourly space velocity of 2.0, a hydrogen circulation rate of 10,000 scf./bbl. and at a peak catalyst bed temperature of 325° C. It will be noted that catalyst bed temperature of Example I was 315° C.

The hydrocracking ability of the non-platinum and non-palladium reference catalyst of Example I was arbitrarily assigned a Relative Hydrocracking Activity of 100. Platinum containing catalysts comprising 0.2 and 0.5 wt. % platinum and palladium containing catalyst comprising 0.4 wt. % palladium hereinafter referred to as Catalysts 5, 6 and 7, respectively, were utilized to hydrocrack the hereinbefore described vacuum gas oil and these three catalysts exhibited a Relative Hydrocracking Activity of 141, 163 and 105, respectively. These data are presented in tabular form in Table III.

TABLE III

| Evaluation for Hydrocracking Activity | | | |
|---|---|---|---|
| Catalyst Identity | 5 | 6 | 7 |
| Platinum Concentration, wt. % | 0.2 | 0.5 | — |
| Palladium Concentration, wt. % | — | — | 0.4 |
| Relative Hydrocracking Activity | 141 | 163 | 105 |

The data presented in foregoing Table III illustrate that a platinum containing catalyst in the claimed critical range, viz, about 0.2 to about 0.5 wt. %, exhibits unexpected and greatly superior catalytic activity when compared with a catalyst containing palladium within the same range. When a Relative Activity comparison of 163 versus 105 can be demonstrated in the realm of catalysis, those skilled in the art will readily recognize the economic advantages afforded through the catalyst of the present invention and the fact that a randomly selected component from a Group VIII or any other group will not necessarily exhibit the desired catalytic characteristics.

These following examples are given to illustrate the preparation of a catalyst composition to be utilized in the process of this invention and its use in the isomerization of isomerizable hydrocarbons. However, these examples are not presented for purposes of limiting the scope of the invention but in order to further illustrate the embodiment of the present process.

EXAMPLE III

This example describes the preparation of a alumina-zeolite-nickel-molybdenum-platinum catalyst which has an extruded carrier material containing 80% alumina and 20% faujasite, 5% nickel, 2% molybdenum and 0.4 weight percent platinum. The extruded alumina-faujasite carrier material is initially impregnated with an aqueous solution containing soluble nickel and molybdenum salts in sufficient concentration to yield a finished catalyst with the desired nickel and molybdenum concentration. The freshly impregnated support is then dried at about 100° C. and calcined at about 500° C. The resulting dried and calcined carrier material containing 5% nickel and 2% molybdenum is impregnated with an aqueous chloroplatinic acid solution with a concentration sufficient to yield a finished catalyst with 0.4 weight percent platinum. The platinum impregnated catalyst is then dried and calcined at 100° C. and 500° C., respectively. The calcined catalyst particles are thereafter reduced in hydrogen for about 1 hour at 550° C. The resulting finished catalyst contains about 1 weight percent chloride.

EXAMPLE IV

A portion of the catalyst produced by the method of Example III is placed in a continuous flow, fixed-bed isomerization plant of conventional design. Substantially pure metaxylene is used as the charge stock. The charge stock is commingled with about 8 moles of $H_2$ per mole of hydrocarbon, heated to about 400° C., and continuously charged to the reactor containing the catalyst which is maintained at about a pressure of about 300 psig. Substantial conversion of metaxylene to para-xylene is obtained . . . i.e. greater than 80 percent of equilibrium.

EXAMPLE V

Another portion of the catalyst produced by Example III is used to isomerize ethylbenzene. The reactor is maintained at 300 psig. and 410° C. as ethylbenzene, commingled with 8 moles of $H_2$ per mole of ethylbenzene is continuously passed to the reactor at 2 LHSV. Substantial conversion of ethylbenzene to the three xylene isomers is observed.

EXAMPLE VI

Another portion of the catalyst produced by Example III is used to isomerize ortho-xylene to para-xylene. The reactor is maintained at a temperature of 400° C., and a pressure of 300 psig. as ortho-xylene, commingled with 8 moles of $H_2$ per mole of ortho-xylene is passed to the reactor at a liquid hourly space velocity (LHSV) of 2.0 hr.$^{-1}$. Substantial conversion—i.e. greater than 80 percent of equilibrium conversion—of ortho-xylene to para-xylene is obtained.

EXAMPLE VII

A catalyst identical to that produced in Example III but containing only 0.40 wt. % combined chloride is used to isomerize 1-butene at a pressure of about 500 psig. and a temperature of about 140° C. in an appropriate continuous isomerization reactor. Substantial conversion to 2-butene is obtained.

EXAMPLE VIII

Another portion of the catalyst utilized in Example VII is charged to an appropriate continuous isomerization reactor maintained at a pressure of about 1000 psig. and a temperature of about 180° C. 3-methyl-1-butene is continuously passed to this reactor and a substantial conversion to 2-methyl-2-butene is obtained.

EXAMPLE IX

Another catalyst identical to that produced in Example III, except that the catalyst particles are contacted with hydrogen fluoride to provide a 2.7 weight percent combined fluoride content, is placed in an appropriate continuous isomerization reactor maintained at a pressure of about 300 psig. and a temperature of about 200° C. Normal hexane is continuously charged to the reactor and an analysis of the product stream shows substantial conversion to 2,2-dimethylbutane, 2,3-dimethylbutane, 2-methylpentane, and 3-methylpentane.

EXAMPLE X

One hundred grams of the reduced catalyst composite of Example III are placed in a glass-lined rotating autoclave along with 75 grams of anhydrous aluminum chloride. The autoclave is sealed, pressured with 25 psi of hydrogen and heated and rotated for 2 hours at 250° C. The autoclave is allowed to cool, depressured through a caustic scrubber, opened and the final composite removed therefrom. Weighing of this composite indicates a 15 wt. percent gain equivalent to the aluminum chloride sublimed and reacted thereon. The caustic scrubber is found to have absorbed hydrogen chloride equivalent to about 5.0 wt. percent of the original composite corresponding to about 0.8 mole of HCl per mole of $ACl_3$ adsorbed.

EXAMPLE XI

A portion of the catalyst of Example X is used to isomerize normal butane at a pressure of 300 psig., a 0.5 hydrogen to hydrocarbon mole ratio, and a 1.0 LHSV at a temperature of 230° C. Substantial conversion of n-butane to isobutane is observed—approximately a conversion of n-butane to isobutane of about 45 wt. % of the butane charge.

EXAMPLE XII

Another portion of the catalyst of Example IX is placed in an appropriate continuous isomerization reactor maintained at a temperature of about 210° C. and a pressure of about 250 psig. Methylcyclopentane is continuously passed to this reactor and a substantial conversion to cyclohexane is observed.

EXAMPLE XIII

A portion of the catalyst prepared in Example III is placed, as a catalytic composite, in a continuous flow fixed bed isomerization plant of conventional design. The charge stock, containing on a weight percent basis, 20% ethylbenzene, 10% para-xylene, 50% meta-xylene and 20% ortho-xylene is commingled with about 8 moles of hydrogen per mole of hydrocarbon, heated to 400° C., and continuously charged at 4 hr.$^{-1}$ liquid hourly space velocity (LHSV) to the reactor which is maintained at a pressure of about 400 psig. and 400° C. The resulting product evidences essentially equilibrium conversion to para-xylene with only insignificant amounts of cracked products thus indicating an efficient alkylaromatic isomerization catalyst.

The foregoing specification and examples clearly illustrate the improvements encompassed by the present invention and the benefits to be afforded a process for the isomerization of hydrocarbons.

I claim as my Invention:

1. A process for isomerizing an isomerizable hydrocarbon which comprises contacting said hydrocarbon, at isomerization conditions, with a catalytic composite comprising a combination of a nickel component, a molybdenum component and a platinum component with a zeolite carrier material wherein said platinum component is present in an amount sufficient to result in the composite containing, on an elemental basis, about 0.2 to about 0.5 percent by weight platinum.

2. The process of claim 1 wherein said zeolitic carrier material comprises faujasite and alumina.

3. The process of claim 1 wherein said isomerizable hydrocarbon is a saturated hydrocarbon and said isomerization conditions include a temperature of about 0° C. to about 425° C. a pressure of about atmospheric to about 100 atmospheres and a liquid hourly space velocity of about 0.1 to about 20.

4. The process of claim 3 wherein said hydrocarbon is commingled with about 0.1 to about 10 moles of hydrogen per mole of hydrocarbon.

5. The process of claim 3 wherein said hydrocarbon is a paraffinic hydrocarbon.

6. The process of claim 5 wherein said hydrocarbon is a $C_4$–$C_9$ alkane.

7. The process of claim 6 wherein said catalytic composite has combined therewith about 1 to about 100 weight percent Friedel-Crafts metal halide, calculated on a metal halide-free composite.

8. The process of claim 1 wherein said hydrocarbon is an olefinic hydrocarbon and said isomerization conditions include a temperature of about 0° C. to about 425° C. and a pressure of about atmospheric to about 100 atmospheres.

9. The process of claim 8 wherein said olefinic hydrocarbon is a $C_4$–$C_9$ isomerizable olefin.

10. The process of claim 1 wherein said isomerizable hydrocarbon is an alkylaromatic hydrocarbon and said isomerization conditions include a temperature of about 0° C. to about 600° C., a pressure of about atmospheric to about 100 atmospheres, and a liquid hourly space velocity of about 0.1 to about 20 hr.$^{-1}$.

11. The process of claim 10 wherein said hydrocarbon is commingled with about 1 to about 25 moles of hydrogen per mole of hydrocarbon.

12. The process of claim 10 wherein said hydrocarbon is a $C_8$ alkylaromatic hydrocarbon or a non-equilibrium mixture of $C_8$ alkylaromatic hydrocarbon.

* * * * *